United States Patent [19]

Janda et al.

[11] Patent Number: 5,418,010

[45] Date of Patent: May 23, 1995

[54] MICROENCAPSULATION PROCESS

[75] Inventors: Joseph Janda, Midlothian; Donald Bernacchi, Chicago; Suzanne Frieders, Oaklawn, all of Ill.

[73] Assignee: Griffith Laboratories Worldwide, Inc., Alsip, Ill.

[21] Appl. No.: 593,678

[22] Filed: Oct. 5, 1990

[51] Int. Cl.$^6$ .................. B01J 13/06; A23L 1/221; A23L 1/222; A23L 1/304

[52] U.S. Cl. .................. 427/213.31; 264/4.1; 264/4.3; 264/4.4; 264/4.6; 424/491; 424/499; 426/96; 426/97; 426/648; 426/650; 426/651; 426/656; 427/213.3; 428/402.2; 428/402.24

[58] Field of Search .............. 264/4.1, 4.3, 4.6, 4.4; 427/213.3, 213.31; 426/96, 464, 656, 518; 424/491, 499; 428/402.2, 402.24

[56] References Cited

U.S. PATENT DOCUMENTS

| | | |
|---|---|---|
| 2,481,413 | 9/1949 | Grisnod . |
| 2,881,076 | 4/1959 | Sair . |
| 3,116,206 | 12/1963 | Brynko et al. . |
| 3,137,631 | 6/1964 | Soloway . |
| 3,406,119 | 10/1968 | Kosar et al. . |
| 3,962,416 | 6/1976 | Katzen . |
| 3,968,268 | 7/1976 | Sair et al. .................. 426/656 X |
| 4,194,013 | 3/1980 | Rehacek et al. . |
| 4,230,687 | 10/1980 | Sair et al. . |
| 4,232,047 | 11/1980 | Sair et al. . |
| 4,551,351 | 11/1985 | Kawasaki et al. .............. 426/656 |
| 4,917,893 | 4/1990 | Okada et al. .................. 428/402.2 |
| 5,145,702 | 9/1992 | Stark et al. .................. 426/656 |
| 5,171,605 | 12/1992 | Attenburrow et al. .......... 426/96 X |
| 5,188,842 | 2/1993 | Visser et al. .................. 426/656 |

*Primary Examiner*—Richard D. Lovering
*Attorney, Agent, or Firm*—Laff, Whitesel, Conte & Saret

[57] ABSTRACT

A microencapsulation process in which a solid or liquid core material is dispersed in a protein slurry, is heated to create a protein melt and then denatured to bring about encapsulation of the core material and the product of that process.

55 Claims, 1 Drawing Sheet

MICROENCAPSULATION PROCESS

BACKGROUND OF THE INVENTION

This invention relates generally to microencapsulation and, more particularly, to microencapsulation of solids and liquids in a water-insoluble protein coating.

Microencapsulation is the an of encapsulating or enclosing a core comprising a solid or liquid in a miniature package called a microcapsule. The encapsulating material or coating of the microcapsule may be of various thicknesses and may be more than one layer thick.

Microcapsules may range from sub-micron in size to several millimeters in size. Although they are often thought of as being smooth and spherical, their shape and surface texture may be quite irregular as determined by both the encapsulating process and the shape and nature of the core material.

In the food industry, for example, microencapsulation is used to stabilize the core material, to control the timing and rate of the release of the core material and to separate reactive or incompatible components of a multicomponent formulation. Thus, microencapsulation makes it possible to protect sensitive food components, to ensure against nutritional loss and to mask or preserve flavors and aromas. Encapsulation also increases stability of vitamin supplements, for example, which are normally sensitive to UV radiation, light, oxygen, metals, humidity and temperature. Microencapsulation is also utilized in the pharmaceutical industry to protect the lining of the mouth and esophagus from harsh, orally administered drugs which are released in the stomach by the action of stomach acids on the microcapsule coating.

Spray drying is one of the most widely used methods of microencapsulation. This process, which involves dispersion and atomization, has a number of drawbacks. One disadvantage of the spray drying microencapsulation technique is that when heat is used for drying, low-boiling point aromatics are lost during the drying process. Another disadvantage is that the core may adhere to the surface of the capsule, presenting a potential for increased oxidation and changes in the flavor balance of the finished food product. Yet another drawback is that the coatings produced ace often water-soluble and temperature sensitive.

Extrusion is an encapsulation method in which a core material is dispersed in an amorphous mass of coating material and ultimately formed into microcapsule. One such method, described in U.S. Pat. No. 4,230,687 which is assigned to the assignee of the present invention, involves a microencapsulation technique in which the core material is mixed with the coating material under conditions of rigorous and intimate mechanical working in the presence of a limited quantity of water and sufficient heat to ensure the formation of a viscous semi-solid homogeneous paste constituting a plastic melt. The melt, which is a homogeneous matrix of the encased core material is formed into a desired shape and dried. The coating agent is a water-soluble or water-dispensable material such as a carbohydrate like dextrin, gum acadia and gum karaya, or a protein like gelatin (water soluble at about 160° F.) or sodium caseinate.

BRIEF DESCRIPTION OF THE DRAWINGS

The features of this invention which are believed to be novel are set forth with particularity in the appended claims. The invention, together with its objects and the advantages thereof, may be best understood by reference to the following description taken in conjunction with the accompanying drawings, in which like reference numerals identify like elements in the several figures and in which:

SUMMARY OF THE INVENTION

Figure 1:
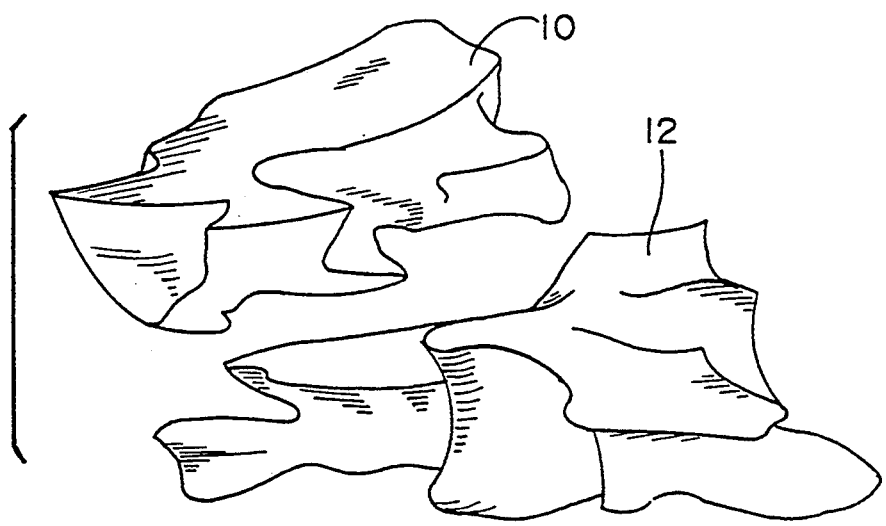
FIG. 1 is a drawing depicting iron core particles approximately 10–20 microns in diameter, under approximately 1000 X magnification.

It is an object of the present invention to provide a method of microencapsulating core material comprising solids and liquids in a water-insoluble protein coating.

It is yet another object of the present invention to provide a method for producing microencapsulated products of a wide range of particle size distributions.

Yet another object of the present invention is to provide a method for producing microcapsules of a predetermined degree of solubility in water.

The present invention therefore comprises a method of preparing microencapsulated particles by:

a) dispersing a core material in a soluble protein slurry;

b) heating the slurry to create a protein melt;

c) denaturing the protein melt to render it insoluble in water, thereby causing the encapsulation of the core material; and d) comminuting the encapsulated core material to provide microcapsules in which the core material is encased in an insoluble protein coating.

In one preferred embodiment, the encapsulated core material of step c) is dried before comminuting.

a. The Core Material

Core materials useful in the practice of the present invention include solids, liquids impregnated in a solid carriers such as sugar, gelatin, or maltodextrin, and liquids standing alone. In the food industry, useful core materials include acidulants, natural colors, flavoring agents and spices, leavening agents, sodium chloride, sweeteners, vitamins, minerals and vitamin precursors (e.g. beta-carotene), flavors, volatile oils and oleoresins. Examples of volatile oils are oil of acacia, oil of cloves, peppermint oil, spearmint oil, lemon oil, garlic oil, and combinations thereof. Examples of oleoresins are ginger, black pepper, and paprika. Typical flavoring agents which may be encapsulated include natural and artificial flavors such as banana, cherry, strawberry, chicken, beef, sweet, savory, and fruit. Encapsulation greatly enhances the stability of these materials, particularly through high temperature/short time processing. Spices, when encapsulated, display enhanced shelf life and enhanced retention of potency, as well as inhibition of reaction with other ingredients.

Acidulants, for example, are used as flavor modifiers, preservation aids and processing aids. Unencapsulated, these materials can react with food ingredients to decrease shelf life, degrade color and flavor, and cause separation of ingredients. Encapsulation precludes or limits oxidation and provides controlled release, thereby minimizing or overcoming many of these problems. Additionally, encapsulation reduces hygroscopicity, reduces dusting and improves flowability. Acidulants that may be encapsulated in accordance with the present invention include all organic and inorganic acids including, in particular, adipic acid, ascorbic acid, citric acid, fumaric acid, lactic acid, malic acid, and acid phosphates.

Vitamins and minerals which are typically added to fortify a variety of foods, including breakfast foods, dairy products, infant formulas and pet foods, may be encapsulated to reduce off-flavors, to permit timed-release and to reduce susceptibility to extremes in temperature and moisture and reactions with other ingredients. Among the vitamins and minerals which may be encapsulated in accordance with the process of the present invention are: ascorbic acid, niacin, vitamin B6, riboflavin, thiamine, vitamin B12, vitamin A, vitamin E, folic acid, vitamin D, phrenic acid, biotin, copper, iron, potassium, zinc, phosphorous, and beta carotin.

The particle size of the core material is dictated by the application. For example, when iron is encapsulated for use as a dietary supplement, bioavailability concerns dictate that the iron core be less than 44 microns in diameter. Iron core particles 10 and 12 approximately 10–20 microns in cross-section are depicted in FIG. 1 under about 1000 X magnification.

b. The Coating

The coatings may be formed from any animal or vegetable protein. The following proteins are preferred as coatings in the practice of the present invention: caseinate, soy concentrate, soy isolate, soy flour, wheat gluten, egg albumen, milk albumen, gelatin, zein (corn protein), and combinations of any two or more of these. Also, cereal proteins can be used, particularly rice gluten, wheat gluten, barley gluten, oat gluten, rye gluten, and sorghum gluten.

c. The Encapsulation Process

The core material to be encapsulated must first be dispersed in an aqueous slurry of the protein coating including water at a level in the range of about 10 to 200% by weight, based on the weight of the core material, with a level of about 50% by weight water preferred. Calcium stearate may optionally be added at a level of about 10 to 30% by weight to improve the pliability of the resulting product. The core material may range from about 5 to 70% by weight, preferably from about 25 to 40% by weight and most preferably at about 30% by weight. Any method of obtaining a uniform dispersion can be used.

In a preferred practice of the present invention, an extruder is used in which the protein and core material are introduced into the extruder feed hopper and dispersed by the vigorous working and shearing action of the rotating extruder screws.

Once a uniform dispersion is obtained, the protein slurry is heated to a temperature sufficient to form a melt. Again, in a preferred embodiment of the invention, the heating step is carried out in an extruder in which the melt is formed under the requisite heating conditions of the extruder.

When the protein is sodium caseinate and the core material is iron at a level of about 30% by weight, a melt may be formed by heating in the temperature range of about 85°–250° F., preferably in the range of about 100°–200° F. and most preferably in the range of about 135°–155° F.

The protein melt is then denatured, which renders it water-insoluble and brings about the encapsulation of the core material. The denaturization may be accomplished with proteolytic enzymes, heat, alkaline agents, or the addition of acid to adjust the pH to the isoelectric point of the protein.

Denaturization either with pH adjustment to the isoelectric point or with proteolytic enzymes is presently preferred in the practice of the invention. When the protein coating is sodium caseinate, and denaturization is carried out by pH adjustment, the pH should be adjusted down to about 6.0, preferably down to about 5.0 and most preferably to about pH 4.6.

Figure 3:
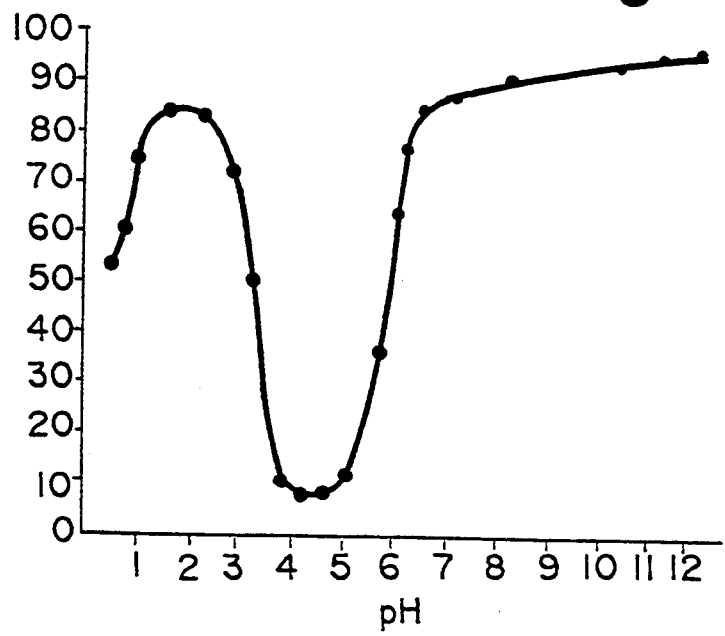
FIG. 3 is a graph illustrating the varying coating solubility achieved by varying the pH of denaturization.

In an alternative embodiment of the invention, denaturization is carried out by adjustment of the pH downwardly to a point short of the isoelectric point of the protein, to tailor the degree of insolubility of the protein to the desired application. FIG. 3 is a graph illustrating the tailoring of the solubility of the coating by varying the pH during denaturization.

In yet another alternate approach, a proteolytic enzyme which renders protein insoluble, such a papain or ficin, may be used. In this approach, the enzyme will typically be used in the form of an aqueous solution containing from about 0.1 to 1.0% by weight of the enzyme and the temperature of the mixture of protein slurry and enzyme will be kept under close control to avoid heat deactivation of the enzyme. Alternatively, partial heat deactivation may be sought in certain circumstances to limit the degree of denaturization to thereby tailor the degree of insolubility of the final encapsulated product.

Figure 2:
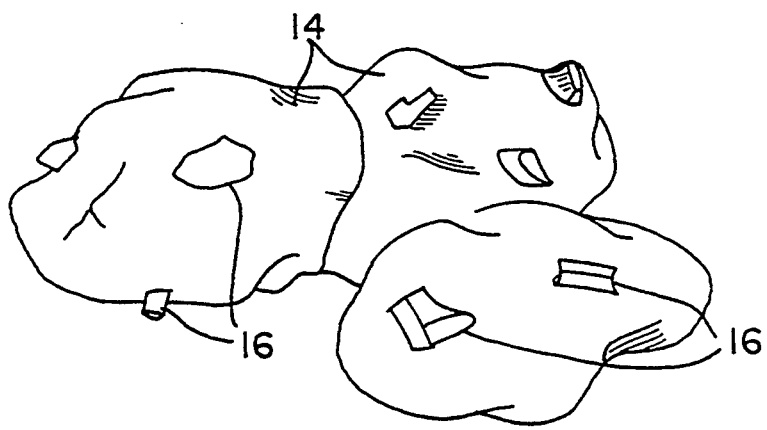
FIG. 2 is a drawing depicting microcapsules of the iron particles of FIG. 1 encased in a protein coating in accordance with the present invention, under approximately 500 X magnification.

Next the encapsulated material is comminuted into a granular form, with the core material remaining encapsulated in the insoluble protein, as illustrated in FIG. 2, in which the coating is depicted by the numeral 14 and iron particles corresponding to those shown in FIG. 1 are depicted by the numeral 16. In a preferred embodiment, the encapsulated material is first dried. Typically drying will be done by heating the material to a temperature below about 350° F. When sodium caseinate is coated on an iron core, the drying temperature should be below about 325° F. and preferably below about 300° F.

Particle size reduction is accomplished by wet milling, for example in a Mikawa mill, by hammer milling of dry material and by centrifugal extrusion.

EXAMPLES

As explained above, the method of the present invention is effective in microencapsulating many different types of core materials in various coatings, over a broad range of concentration ratios of coatings to core material. In the illustrative examples which follow, the ratio of coating to core material, in parts by weight, embraces the range of from about 5 to about 70. Since the objectives of the present invention can be accomplished with conventional equipment, including commercially available mixers and extruders, no detailed description of the apparatus is provided. Rather, the following examples are described with reference to various types of suitable, commercially available equipment.

EXAMPLE 1

In this example, particulate iron of from about 10 to 20 microns in diameter, as illustrated in FIG. 1, was dispersed in a soluble protein slurry of sodium caseinate, by blending in a ribbon blender. The mixture also contained calcium stearate to improve pliability of the end product and various colorants. The slurry comprised the following levels of these components, in percentages by weight:

| Iron | 30.0% |
|---|---|
| Calcium Stearate | 10.0 |
| Sodium Caseinate | 49.1 |
| Titanium Dioxide | 10.0 |
| Yellow #6 (17%) | .72 |
| Yellow #5 (25%) | 4.0 |
| | 100% |

Once the core material was dispersed in the slurry using a Baker-Perkins extruder (a twin screw extruder), the slurry was heated to about 90° F. to create a protein melt. The protein melt was then denatured (and hence precipitated) by adding sufficient hydrochloric acid to adjust the pH down to about pH 4.6. The denatured protein was then wet ground in a Mikawa mill to reduce average particle size to about 180 microns, which in turn reduced the drying time.

The precipitate was then dried by heating in a pan drier to 300° F. for about 20 minutes and the dried precipitate was further comminuted in a hammer mill into a granular form having an average particle size of about 90 microns. The resulting product, illustrated in FIG. 2, comprised iron particle microcapsules with about 85% encapsulation.

EXAMPLE 2

In this example, mixtures of soluble proteins and soluble carbohydrates are examined as the encapsulating matrix. Thus, if sodium caseinate is combined with hydrolyzed cereal solids in a ratio of about one to one by weight, and the process of Example 1 were carried out using this protein/carbohydrate combination with a flavoring agent such as oil of cloves at the core, a controlled flavor release would result when the encapsulated material is placed in a aqueous media.

EXAMPLE 3

Another technique for controlling the solubility of the coating of the microcapsule is examined in this example. Thus, if the method of Example 1 were followed but the pH during the denaturing process were adjusted to about pH 5.6, the coating would be partially soluble in water. Such a product would have about a 35 percent by weight solubility in water, as seen in FIG. 3.

EXAMPLE 4

Yet another technique for controlling the solubility of the coating is explored in this example, namely varying the temperature and/or the use during denaturization with a proteolytic enzyme. Thus, the procedure of Example 1 could be generally followed but denaturization carried out using ficin at pH of 5.5, to achieve a tailored solubility. Alternatively, if an activator such as cystine, or a chemical inhibitor such as sorbic acid could be used to tailor the solubility.

EXAMPLE 5

In this Example, a series of alternative solid and liquid core materials as well as a variety of coatings are set out in formulas which, if combined in accordance with the practice of Example 1 would produce useful microencapsulated products in accordance with the present invention. All figures are in percentages by weight.

| I. | |
|---|---|
| Soy Protein Isolate | 64 |
| Calcium Stearate | 10 |
| Iron | 25 |
| TiO$_2$ | 1.0 |
| II. | |
| Soy Protein Concentrate | 64 |
| Calcium Stearate | 10 |
| Iron | 25 |
| TiO$_2$ | 1.0 |
| III. | |
| Egg Whites (Dried) | 64 |
| Calcium Stearate | 10 |
| Iron | 25 |
| TiO$_2$ | 1.0 |
| IV. | |
| Sodium Caseinate | 63 |
| Calcium Stearate | 10 |
| TiO$_2$ | 20 |
| Beta Carotene (30%) | 2.0 |
| Caramel Color | 5.0 |
| V. | |
| Vitamin Premix | 25 |
| Calcium Stearate | 10 |
| Sodium Caseinate | 50.6 |
| TiO$_2$ | 14 |
| Yellow #6 | 0.4 |
| VI. | |
| Magnesium Chloride (Anhydrous) | 12.5 |
| Zinc Stearate | 10.0 |
| Encapsulating Protein | 77.5 |
| VII. | |
| Copper Gluconate | 5.0 |
| Calcium Stearate | 10.0 |
| Encapsulating Protein | 85.0 |
| VIII. | |
| Oil of Orange | 20.0 |
| Calcium Stearate | 10.0 |
| Encapsulating Protein | 70.0 |

While the present invention is described above in connection with the preferred or illustrative embodiments, those embodiments are not intended to be exhaustive or limiting of the invention. Rather, the invention is intended to cover any alternatives, modifications or equivalents that may be included within its sphere and scope, as defined by the appended claims.

What we claim is:

1. A method of microencapsulating a core material comprising:
   a) dispersing the core material in a protein slurry;
   b) heating the slurry to create a protein melt;
   c) denaturing the protein melt by treating the protein melt with acid to adjust the pH to the isoelectric point of the protein, thereby causing encapsulation of the core material; and
   d) comminuting the encapsulated core material to provide microcapsulates.

2. The method of claim 1 wherein the core material is chosen from the group consisting of solids, liquids, and liquids impregnated in solid carriers.

3. The method of claim 1 wherein the core material is chosen from the group consisting of acidulants, natural colors, flavoring agents, spices, leavening agents, sweeteners, vitamins, minerals, vitamin precursors, and oleoresins.

4. The method of claim 1 wherein the core material is chosen from the group consisting of oil of acacia, oil of cloves, peppermint oil, spearmint oil, lemon oil, garlic oil, and combinations thereof.

5. The method of claim 1 wherein the core material is chosen from the group consisting of ginger, black pepper, and paprika.

6. The method of claim 1 wherein the core material is chosen from the group consisting of natural and artificial flavors of chicken, beef, savory, and fruit.

7. The method of claim 1 wherein the core material is chosen from the group consisting of adipic acid, ascorbic acid, citric acid, fumaric acid, lactic acid, malic acid, and acid phosphate.

8. The method of claim 1 wherein the core material is chosen from the group consisting of ascorbic acid, niacin, vitamin B6, riboflavin, thiamine, vitamin B12, vitamin A, vitamin E, folic acid, vitamin D. phrenic acid, biotin, copper, iron, potassium, zinc, phosphorous, beta carotin, and combinations of two or more thereof.

9. The method of claim 1 wherein the core material is iron particles.

10. The method of claim 9 in which the iron particles are less than 44 microns in diameter.

11. The method of claim 1 in which the protein of the protein slurry is chosen from the group consisting of caseinate, soy concentrate, soy isolate, soy flour, wheat gluten, egg albumen, milk albumen, gelatin, zein, rice gluten, barley gluten, oat gluten, rye gluten, and sorghum gluten, and combinations of two or more thereof.

12. The method of claim 1 in which the protein of the protein slurry is caseinate.

13. The method of claim 1 in which the protein slurry includes water at a level in the range of about 10 to 200% by weight, based on the weight of the core material.

14. The method of claim 1 in which the protein slurry includes water at a level of about 50% by weight, based on the weight of the core material.

15. The method of claim 1 in which calcium stearate is added at a level of about 10 to 30% by weight, based on the weight of the core material.

16. The method of claim 1 in which the core material is present in a range of about 5 to 70% by weight based upon the weight of the slurry.

17. The method of claim 1 in which the core material is present in a range of about 25 to 40% by weight based upon the weight of the slurry.

18. The method of claim 1 in which the core material is present at about 30% by weight based upon the weight of the slurry.

19. The method of claim 1 in which the core material is dispersed in the protein slurry using an extruder.

20. The method of claim 1 in which the protein slurry containing the core material is heated in an extruder to create a protein melt.

21. The method of claim 1 in which the protein is sodium caseinate and the core material is iron.

22. The method of claim 21 in which the iron is present at a level of about 30% by weight and the melt is formed by heating in the temperature range of about 85°–250° F.

23. The method of claim 22 in which the melt is formed by heating in the temperature range of about 100°–200° F.

24. The method of claim 22 in which the melt is formed by heating in the temperature range of about 135°–155° F.

25. The method of claim 1 in which the protein of the protein slurry is sodium caseinate and denaturization is carried out by adjusting the pH of the protein melt to about pH 5.0.

26. The method of claim 1 in which the protein of the protein slurry is sodium caseinate and denaturization is carried out by adjusting the pH of the protein melt to about pH 4.6.

27. The method of claim 1 in which the protein melt is dried before comminuting.

28. The method of claim 27 in which the drying is accomplished by heating to a temperature sufficient to dry the protein melt and less than about 350° F.

29. A method of microencapsulating a core material comprising:
 a) dispersing the core material in a protein slurry;
 b) heating the slurry to create a protein melt;
 c) denaturing the protein melt by adjusting the pH downwardly to a point short of the isoelectric point of the protein, thereby tailoring the degree of the insolubility of the protein and causing encapsulation of the core material; and
 d) comminuting the encapsulated core material to provide microcapsules.

30. The method of claim 29 wherein the core material is chosen from the group consisting of solids, liquids, and liquids impregnated in solid carriers.

31. The method of claim 29 wherein the core material is chosen from the group consisting of acidulants, natural colors, flavoring agents, spices, leavening agents, sweeteners, vitamins, minerals, vitamin precursors, and oleoresins.

32. The method of claim 29 wherein the core material is chosen from the group consisting of oil of acacia, oil of cloves, peppermint oil, spearmint oil, lemon oil, garlic oil, and combinations thereof.

33. The method of claim 29 wherein the core material is chosen from the group consisting of ginger, black pepper, and paprika.

34. The method of claim 29 wherein the core material is chosen from the group consisting of natural and artificial flavors of banana, cherry, strawberry, chicken, beef, savory, and fruit.

35. The method of claim 29 wherein in the core material is chosen from the group consisting of adipic acid, ascorbic acid, citric acid, fumaric acid, lactic acid, malic acid, and acid phosphate.

36. The method of 29 wherein in the core material is chosen from the group consisting of ascorbic acid, niacin, vitamin B6, riboflavin, thiamine, vitamin B12, vitamin A, vitamin E, folic acid, vitamin D, phrenic acid, biotin, copper, iron, potassium, zinc, phosphorous, beta carotin, and combinations of two or more thereof.

37. The method of claim 29 wherein in the core material is iron particles.

38. The method of claim 37 in which the iron particles are less than 44 microns in diameter.

39. The method of claim 29 in which the protein of the protein slurry is chosen from the group consisting of caseinate, soy concentrate, soy isolate, soy flour, wheat gluten, egg albumen, milk albumen, gelatin, zein, rice gluten, barley gluten, oat gluten, rye gluten, and sorghum gluten, and combinations of two or more thereof.

40. The method of claim 29 in which the protein of the protein slurry is caseinate.

41. The method of claim 29 in which the protein slurry includes water at a level in the range of about 10 to 200% by weight, based on the weight of the core material.

42. The method of claim 29 in which the protein slurry includes water at a level of about 50% by weight, based on the weight of the core material.

43. The method of claim 29 in which calcium stearate is added at a level of about 10 to 30% by weight, based on the weight of the core material.

44. The method of claim 29 in which the core material is present in a range of about 5 to 70% by weight based upon the weight of the slurry.

45. The method of claim 29 in which the core material is present in a range of about 25 to 40% by weight based upon the weight of the slurry.

46. The method of claim 29 in which the core material is present at about 30% by weight based upon the weight of the slurry.

47. The method of claim 29 in which the core material is dispersed in the protein slurry using an extruder.

48. The method of claim 29 in which the protein slurry containing the core material is heated in an extruder to create a protein melt.

49. The method of claim 29 in which the protein is sodium caseinate and the core material is iron.

50. The method of claim 49 in which the iron is present at a level of about 30% by weight and the melt is formed by heating in the temperature range of about 85°–250° F.

51. The method of claim 50 in which the melt is formed by heating in the temperature range of about 100°–200° F.

52. The method of claim 50 in which the melt is formed by heating in the temperature range of about 135°–155° F.

53. A method of microencapsulating a core material comprising:
 a) dispersing the core material in a protein slurry;
 b) heating the slurry to create a protein melt;
 c) denaturing the protein melt by treating the protein melt with a proteolytic enzyme chosen from the group consisting of papain and ficin, thereby causing encapsulation of the core material; and
 d) comminuting the encapsulated core material to provide microcapsules.

54. The method of claim 53 in which the proteolytic enzyme is used in the form of an aqueous solution containing from about 0.1 to about 1.0% by weight of the enzyme.

55. The method of claim 53 in which the enzyme is partially heat deactivated to limit the degree of denaturization, thereby to tailor the degree of insolubility of the final encapsulated product.

* * * * *